United States Patent [19]

Miyazawa

[11] 4,376,951

[45] Mar. 15, 1983

[54] FOREIGN MATTER DETECTING DEVICE

[75] Inventor: Takashi Miyazawa, Funabashi, Japan

[73] Assignee: Kirin Beer Kabushiki Kaisha, Tokyo, Japan

[21] Appl. No.: 206,219

[22] Filed: Nov. 12, 1980

Related U.S. Application Data

[63] Continuation-in-part of Ser. No. 77,242, Sep. 19, 1979, abandoned.

[30] Foreign Application Priority Data

Sep. 29, 1978 [JP] Japan .............................. 53-120073

[51] Int. Cl.³ ............................................ H04N 7/18
[52] U.S. Cl. .............................. 358/106; 250/223 B; 250/572; 209/939; 356/237; 356/240; 356/430
[58] Field of Search .................. 358/106, 93; 356/240, 356/430, 237; 209/939; 250/223 B, 572

[56] References Cited

U.S. PATENT DOCUMENTS

| Re. 28,984 | 9/1976 | Drinkuth | 358/106 |
| 2,636,602 | 4/1953 | Stoate | 358/106 |
| 3,746,784 | 7/1973 | Van Oosterhout | 358/106 |
| 3,777,169 | 12/1973 | Walter | 358/106 |
| 3,811,567 | 5/1974 | Tomita | 358/106 |
| 3,877,821 | 4/1975 | Price | 358/106 |
| 3,932,042 | 1/1976 | Faani | 358/106 |
| 3,992,571 | 11/1976 | Garlick | 358/106 |
| 4,002,823 | 1/1977 | Van Oosterhout | 358/106 |
| 4,136,930 | 1/1979 | Gomm | 358/106 |
| 4,280,624 | 7/1981 | Ford | 209/939 |

Primary Examiner—Howard Britton
Attorney, Agent, or Firm—Ladas & Parry

[57] ABSTRACT

In general, used beer, alcoholic drink, soft drink or medical bottles are collected to be used again. Such used returnable bottles often have foreign matters or contaminants such as dust and leavings or cracks, and they must be removed from the bottling line before or after the bottle cleaning process. This invention positively satisfies such a requirement. The foreign matter detecting device comprises: a photoelectric conversion device having a number of light receiving elements; and a video signal processing device for successively subjecting to comparison and discrimination the detection signals of variable two adjacent points which are detected by the photoelectric conversion device, to determine whether or not the bottle has a foreign matter.

16 Claims, 38 Drawing Figures

CLOCK PULSE

INPUT OF SHIFT REGISTER

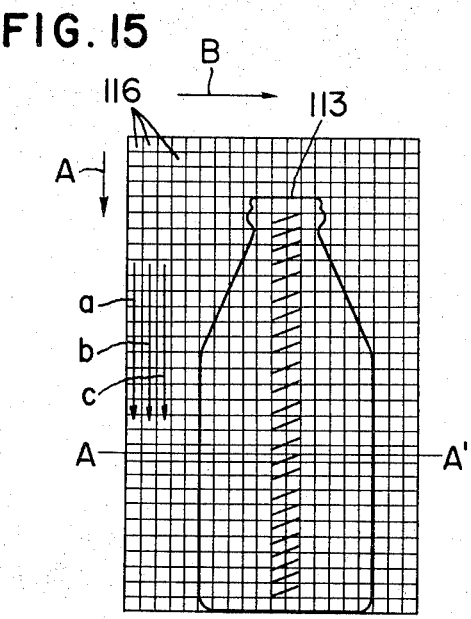
FIG. 15
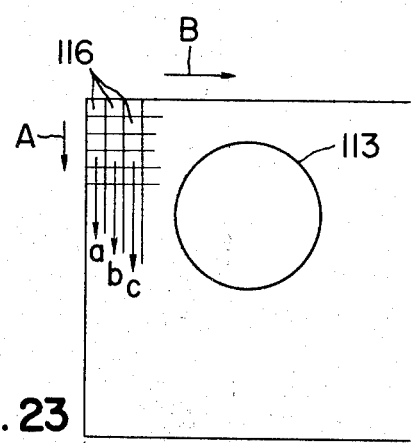
FIG. 22
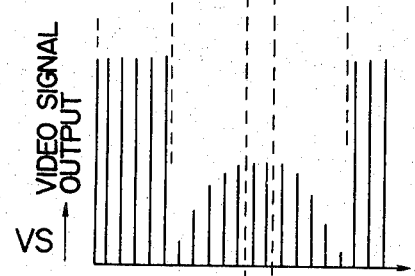
FIG. 16
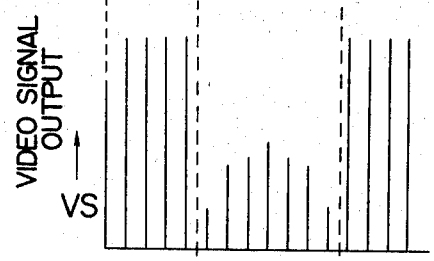
FIG. 23
FIG. 17
FIG. 18
FIG. 19
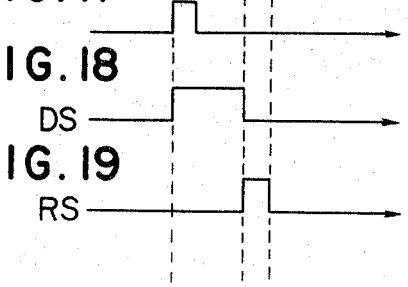
FIG. 24
FIG. 25
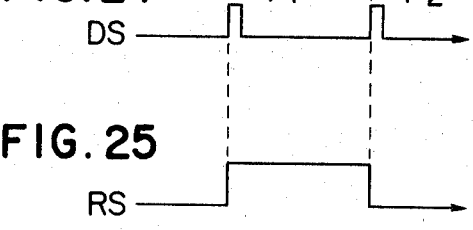

FOREIGN MATTER DETECTING DEVICE

CROSS-REFERENCE TO RELATED APPLICATION

This application is a continuation in part of our prior application Ser. No. 077,242, filed Sept. 19, 1979, entitled FOREIGN MATTER DETECTING DEVICE, and now abandoned.

BACKGROUND OF THE INVENTION

This invention relates to a foreign matter detecting device which optically detects whether or not objects to be inspected such as beverage or medical bottles have foreign matters such as dust or leavings or cracks.

In general, returnable bottles (used beer, alcoholic, soft drink, food bottles or medical bottles) are collected to be used again. In this connection, such used returnable bottles are cleaned with a bottle cleaning device to remove the foreign matters. However, sometimes it is difficult for the bottle cleaning device to completely remove foreign matters strongly stuck to the bottle. Therefore, such bottle must be removed from the bottling line before or after the bottle cleaning process.

Although it is sufficient at low speed about 100 bottles per a minute to inspect producing bottles which are produced in a manufacturing factory, it is requested to inspect at high speed about 1,000 bottles per a minute concerning the above returnable bottles. This is based on that the transfer speed of the bottling line is higher than that of the producing line of the bottles. Further, although objects of inspection concerning the above producing bottles are cracks, bubbles and birdswings, objects of inspection concerning the returnable bottles are contaminants and foreign matters including cracks, bubbles and so on, and the scope of the objects is broader than that of the producing bottles. As described above, there are some difficult problems concerning the inspection of the returnable bottles. In addition, it is requested to detect a smaller size foreign matter or contaminant, e.g. about 0.5 mm-1.0 mm, for the returnable bottles.

By the way, two kinds of foreign matter detecting devices, one for inspecting the body (barrel) of a bottle and the other for inspecting the bottom, are known in the art. In the former device, light is externally applied to the bottle while the bottle being rotated, and light passed through the bottle is detected by a photoelectric element inserted thereinto. That is, the photoelectric element is employed to compare the quantity of transmission light obtained when a certain region of the bottle has a foreign matter to the quantity of transmission light obtained when the certain region has no foreign matter, whereby the entire body of the bottle is inspected for a foreign matter. However, the detecting device is disadvantageous in the following points: As the bottle is rotated at a high speed, the apparatus itself is liable to become bulky and mechanically complicated, and the foreign matter detecting accuracy is low and inspection speed is also very low. Furthermore, since it is necessary to insert the photoelectric element into the bottle, the air in the bottle may be contaminated, which causes a problem in food hygiene.

Further known in the art is a foreign matter detecting device in which a light source is provided on one side of a bottle to be inspected which is being rotated at high speed, to irradiate it, and a television camera using an accumulation type image pickup tube is provided on the opposite side of the bottle, to inspect the bottle. In the detecting device, the position of a bottle to be inspected is mechanically detected, and the entire bottle is inspected with one scanning line. However, the detecting device is also disadvantageous in the following points: Since the position of a bottle to be inspected is mechanically detected as described above, an error is liable to be involved in position detection, and it is difficult to uniformly inspect the surface of the bottle. Furthermore, it is impossible for one television camera to inspect two bottles or more simultaneously. Accordingly, it is difficult to increase the inspection speed. In addition, as the bottle is rotated at high speed, the device is liable to become bulky, and the mechanical handling system becomes very heavy and difficult to maintain.

In order to overcome these difficulties, a foreign matter detecting device has been proposed in the art, in which light is externally applied to a bottle which is conveyed by a conveyer and is being rotated at low speed, and a television camera provided on the opposite side of the bottle is used to inspect the entire body of the bottle. However, it is difficult to inspect bottles with high accuracy. In the end portions of the bottle, or in the portion other than the central portion of the bottle where characters or marks curved in relief are provided or the glass wall thickness is not uniform or a joint is provided, the optical path of light passed through such portions is increased or shadows are created by optical refraction, as a result of which a signal similar to that provided by a foreign matter on the bottle is produced, which makes it difficult to inspect the bottle with high accuracy.

Furthermore, a foreign matter detecting device provided with an accumulation type image pickup tube and using an electric flash as the light source is proposed in the art. However, the device still suffers from the following problems: Because of the after-image phenomenon of the image pickup tube, it is difficult to increase the inspection speed. It is necessary to frequently change the electric flash. It is still difficult to inspect with high accuracy the peripheral portions of the bottle where characters or marks curved in relief are provided and a joint is provided.

SUMMARY OF THE INVENTION

Accordingly, a first object of this invention is to eliminate all of the above-described difficulties accompanying a conventional foreign matter detecting device.

A second object of the invention is to provide a novel foreign matter detecting device simple in construction and low in manufacturing cost, which can readily detect foreign matters and contaminants on a returnable bottle with high accuracy, thus contributing to labor saving in inspecting bottles.

A third object of the invention is to provide a novel foreign matter detecting device which can freely detect various foreign matters by selecting a comparison distance of two adjacent points subjected to comparison and discrimination.

A fourth object of the invention is to provide a foreign matter detecting device in which an inspection region is automatically determined from a video signal concerning an object to be inspected such as a bottle, and the region is subjected to surface inspection with high accuracy.

A fifth object of the invention is to provide a foreign matter detecting device in which an inspection region is determined in a direction perpendicular to or in parallel with the axis of an object to be inspected.

The novel features which are considered characteristic of this invention are set forth in the appended claims. This invention itself, however, as well as other objects and advantages thereof will become more apparent from the following detailed description of illustrative embodiments, when read in conjunction with the accompanying drawings, in which like parts are designated by like reference numerals.

BRIEF DESCRIPTION OF THE DRAWINGS

In the accompanying drawings:

FIG. 15 shows the image of a bottle to be inspected, which is formed on the elements of the CCD incorporated in the foreign matter detecting device;

FIG. 16 is a graphical representation indicating the output levels of video signals outputted by the CCD elements provided along the line A—A' in FIG. 15;

FIG. 17 shows a bottle end signal outputted by a bottle end detecting circuit in the foreign matter detecting device in FIG. 14;

FIG. 18 shows a pulse waveform of a delay circuit such as a one-shot multivibrator;

FIG. 19 shows an inspection region signal from an inspection region signal generating circuit;

FIG. 22 shows the image of a bottle to be inspected, which is formed on the CCD elements in the detecting device;

FIG. 23 shows the output levels of video signals corresponding to FIG. 22;

FIG. 24 shows one example of a bottle end detection signal corresponding to FIG. 23;

FIG. 25 shows one example of an inspection region signal corresponding to FIG. 24;

DETAILED DESCRIPTION OF THE INVENTION

Figure 1:
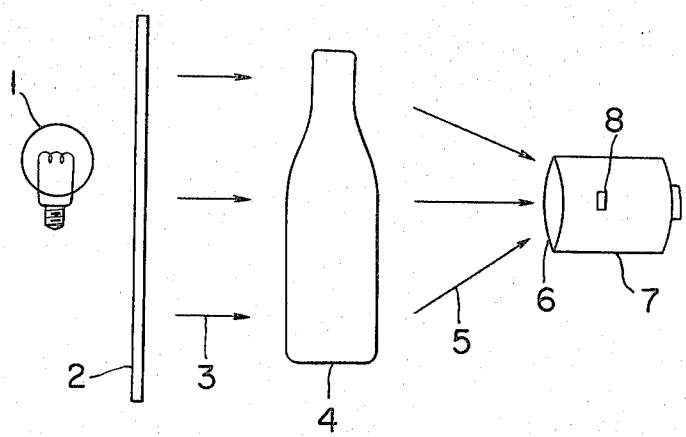
FIG. 1 is an explanatory diagram for a description of the principle of a foreign matter detecting device according to this invention.

FIG. 1 is a diagram for a description of the principle of a foreign matter detecting device according to this invention. Light emitted by a light source 1 is diffused by a diffusing plate 2, as a result of which diffusion light 3 is projected onto an empty bottle 4. Light 5 passed through the empty bottle 4 is condensed by a condenser 6 and is then irradiated on a photoelectric conversion device 8 such as a charge coupled device incorporated in a camera box, so that the image of the bottle is formed on the light receiving surface of the device 8.

Figure 2:
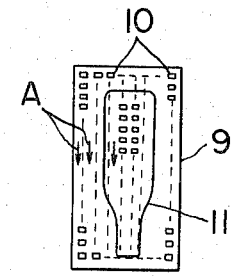
FIG. 2 is a diagram showing a charge coupled device forming a photoelectric conversion device incorporated in the foreign matter detecting device of the invention.

The photoelectric conversion device 8 comprises a number of light receiving elements arranged as shown in FIG. 2. More specifically, a charge coupled device (hereinafter referred to merely as "a CCD" when applicable) 9 has, for instance, several thousands to several hundred thousands of elements 10 which provide output signals proportional to quantities of incident light. A device (not shown) for successively delivering the output signals of the elements 10 is provided in the CCD 9. Thus, as the output signals of the elements 10 are successively delivered, the entire surface of the body of the bottle is scanned. If the bottle contains a foreign matter, the quantity of light applied to the element or elements corresponding to the position of the foreign matter is decreased. Accordingly, the presence or absence of a foreign matter can be detected by detecting the decrease of the quantity of incident light.

The detection signals are delivered from the elements 10 of the CCD 9 by vertically scanning the elements 10, the scanning being started with the leftmost column thereof. The entire image 10 of the bottle formed on the CCD element surface is scanned.

A device 13 for processing the detection signals provided by the photoelectric conversion device 8 will be described with reference to FIG. 3.

The video detection signal outputted by the photoelectric conversion device 8 is applied to an analog-to-digital converter (hereinafter referred to as "an A/D converter" when applicable) 14 so that it can be readily processed. In the A/D converter 14, the detection signal is converted into a digital signal. The digital signals thus obtained are applied directly or through a register 15 to a comparator 16 where the magnitudes of digital signals corresponding to two adjacent points are subjected to comparison and discrimination. Accordingly, when the difference between the two signals is more than a predetermined permissive value, the presence or absence of a foreign matter can be positively detected by detecting the output signals.

The digital signals corresponding to variable two points are successively subjected to comparison by the comparator 16 as described above. This is due to the following reason: There are a variety of bottles; that is, bottles are different in type, kind, color, shape, thickness, etc. Accordingly, the quantities of light passed through different bottles are different. In addition, the quantity of light passed through a bottle is affected by characters curved in relief thereon. These factors make it difficult to discriminate or detect the presence or absence of foreign matter in the bottle. In order to minimize these effects, the digital signals corresponding to variable two points are successively compared. When the CCD 9 scans along the axis of a bottle, the variation in light quantity between variable two points of the bottle body, which correspond to adjacent elements 10 of the CCD 9, is relatively small. By utilizing this fact, the detection of a foreign matter is carried out according to the magnitude of variation in light quantity passed through the above-described variable two points.

Figure 3:
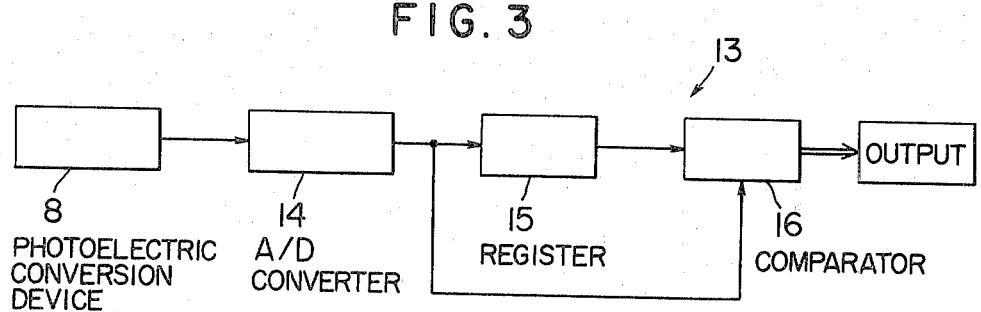
FIG. 3 is a block diagram illustrating a video signal processing device adapted to process a detection signal detected by the photoelectric conversion device.
Figure 4:
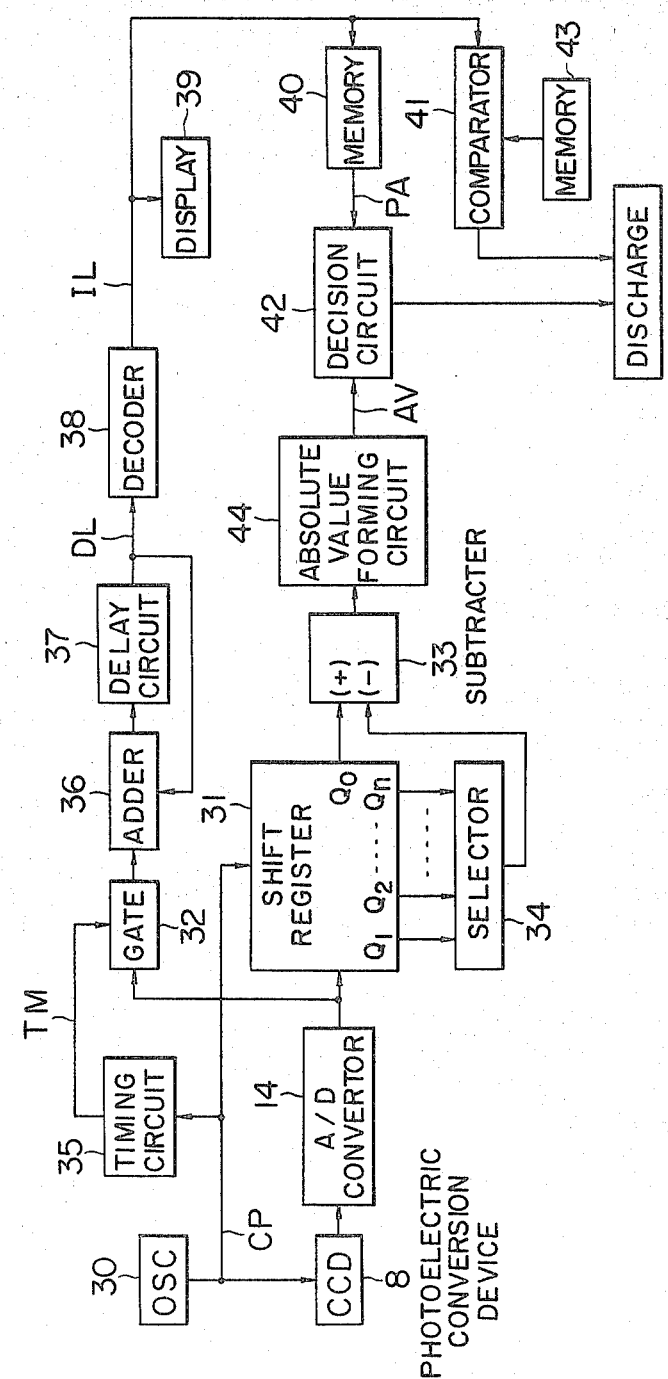
FIG. 4 is a block diagram which more specifically illustrates a device shown in FIG. 3.
Figure 5A:
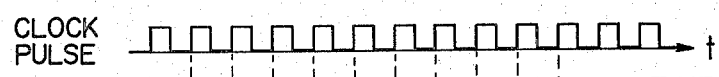
FIGS. 5(A) through 5(C) show one example of operation of the apparatus illustrated in FIG. 4, respectively.
Figure 5B:
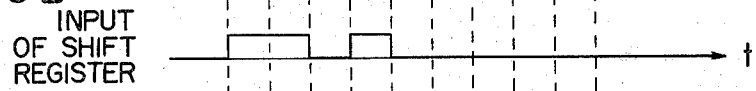
Figure 5C:
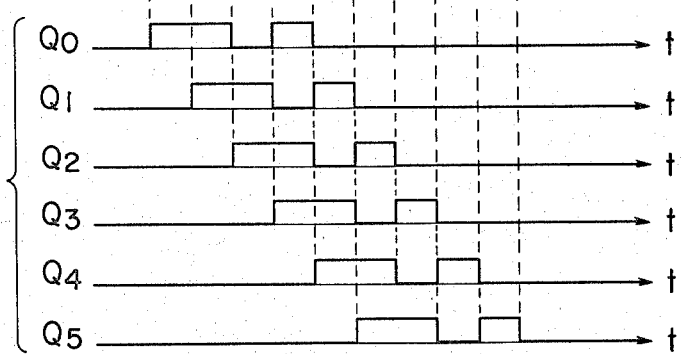

The detailed diagram of the circuit shown in FIG. 3 is as shown in FIG. 4. As shown in FIG. 4, clock pulse CP (see FIG. 5(A)) are sent to CCD 8 at a stable frequency from an oscillator 30, and the photoelectric signal is inputted to an A/D converter 14 to be converted to the series digital signal as shown in FIG. 5(B). Then, the series digital signal is inputted to a shift register 31 and a gate 32. The output terminals $Q_0$-$Q_n$ of the shift register 31 output signals shifted by one bit as shown in FIG. 5(C) in synchronization with the clock pulse CP. While the output $Q_0$ is inputted to the positive terminal (+) of a subtracter 33, one of the other outputs $Q_1$-$Q_n$ is selected by a selector 34 to be inputted to the negative terminal (−) of the subtracter 33. The subtracter 33 determines the difference between the both inputs, and the difference is converted to an absolute value signal AV in an absolute value forming circuit 44. When the polarity of the digital value is positive, the digital value signal as it is, is outputted. On the other hand, when negative, the digital value remains unchanged, and an absolute value signal is outputted by converting only the porality.

The clock pulse CP is inputted to a timing circuit 35, and the timing circuit 35 forms timing pulse TM with a predetermined pulse width, to send to a gate 32. Thus, when a timing pulse TM opens the gate 32, the output of the A/D converter 14 is supplied to the adder 36 to be added with the output DL of a delay circuit 37. The time delay in the delay circuit 37 is the time corresponding to one pulse of the clock pulse CP. The adder 36 is in operation while the gate 32 is open, and is out of operation while the gate 32 is closed. Accordingly, the output of the adder 36, i.e., the output DL of the delay circuit 37 indicates the total of the magnitude of the quantity signal of light passed through the object (hereinafter referred to as "transmitted light signal") when the gate 32 is open. The signal DL is decoded by a decoder 38 to be inputted as the transmitted light signal IL to a display 39, a memory 40 and a comparator 41. Then, the display 39 indicates the determined amount of transmitted light, and the memory 40 outputs the permissive absolute value PA which has been stored in advance therein, in response to the inputted amount of transmitted light. The permissive absolute value PA is inputted to a decision circuit 42 for quantitative comparison with the absolute value signal AV formed by the absolute value forming circuit 44. The decision circuit 42 outputs the discharge signal, judging a foreign matter is detected when the absolute value signal AV is larger than the permissive absolute value PA. Then, the relevant object is discharged. In addition the minimum amount of light transmitted through the object is stored in advance in the memory 40. The comparator 41 compares the transmitted light signal IL with the minimum amount, and outputs the discharge signal, judging impossible to detect when the former is smaller than the latter, that is, when the total amount of the light transmitted through the whole inspected object is extremely small. Then, the inspected object is discharged. It makes possible discharge of the inspected object without the discharge signal from the decision circuit 42. The memory 40 stores different permissive absolute values PA comparative with each of the transmitted light signal IL (e.g., ten levels); i.e., the permissive absolute value PA is "4" for the transmitted light signal IL, 10; "8", "3".

Figure 6A:
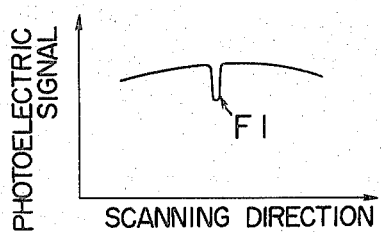
FIGS. 6(A) through 6(C) are explanatory graphs for description of the principle of the apparatus according to this invention, respectively.
Figure 6B:
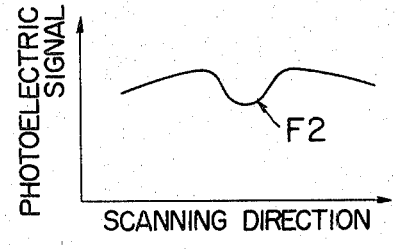
Figure 6C:
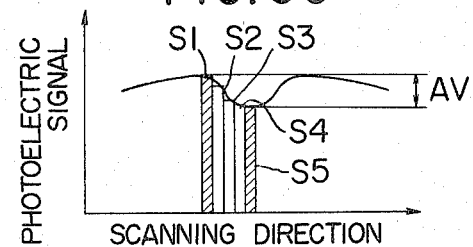

The selector 34 can selectively input the outputs $Q_1$-$Q_n$ from the shift register 31 to the subtracter 33. For detection of the foreign matter which generates a sharp change of the signal as shown in FIG. 6(A), $F_1$, the output $Q_1$ immediately adjacent the output $Q_0$ is selected. As shown in FIG. 6(C), the difference between variable two points immediately adjacent each other, such as between scanning regions $S_1$ and $S_2$; $S_2$ and $S_3$; and $S_3$ and $S_4$, is successively selected. Thus, a large difference can be accurately determined for the abrupt signal change. For detection of the foreign matter which generates a blunt signal change, the output $Q_4$ ($Q_3$ or $Q_5$) is away from the output $Q_0$ by a few scanning regions is selected. As shown in FIG. 6(C) $F_2$, the difference between variable two neighboring points, such as scanning regions $S_1$ and $S_5$; $S_2$ and $S_6$; and $S_3$ and $S_7$, is selected in sequence. Thus, a large difference (AV) is accurately determined for the blunt signal change.

The above-described foreign matter detecting device will be further described with reference to the case where it is applied to an actual bottling line.

Figure 7:
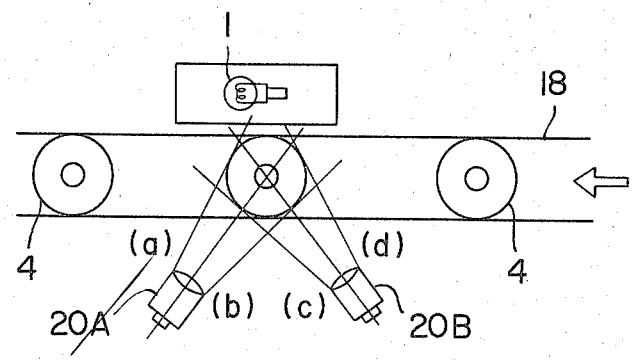
FIG. 7 is a diagram showing the foreign matter detecting device installed on the actual bottling line.

FIG. 7 is a plan view of the foreign matter detecting device provided on the bottling line. Empty bottles 4, 4, ... to be used again are conveyed by a conveying belt 18 at predetermined intervals. Foreign matters on the bottles 4 are detected by the detecting device; however, it is rather difficult for the device to detect foreign matters on the end portion of a bottle. In order to overcome this difficulty, two CCD cameras 20A and 20B may be disposed to form an angle, for instance 90 degrees, with respect to a bottle, so that the CCD camera 20A covers the range a–b while the CCD camera 20B covers the range c–d; that is, the entire body of the bottle is detected by the two CCD cameras 20A and 20B. Each of the CCD cameras is similar to that shown in FIG. 1; that is, a condenser lens and a CCD are incorporated in a camera box.

Figure 8:
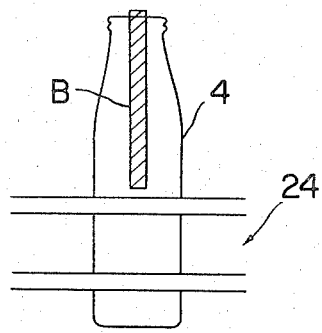
FIG. 8 shows a mechanism for rotating empty bottles.
Figure 9:
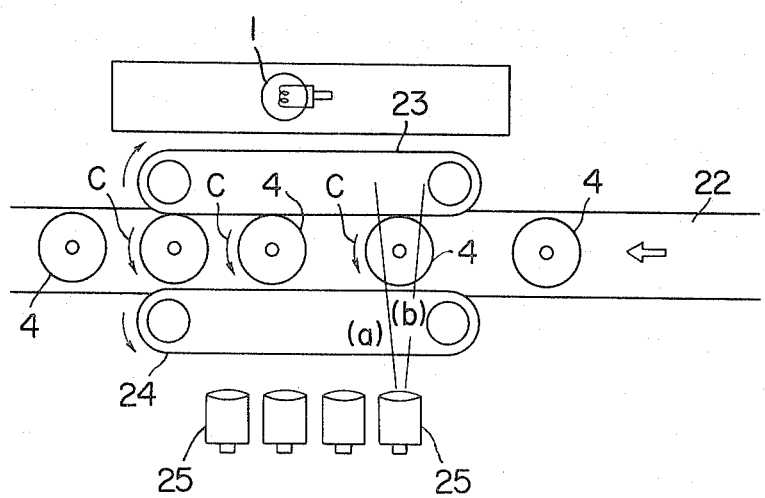
FIG. 9 is an explanatory diagram showing one example of the foreign matter detecting device provided with the bottle rotating mechanism.

A method of most effectively detecting the mouth portion and the character-in-relief portion of a bottle with the foreign matter detecting device is as shown in FIG. 8, in which the detection is effected with the bottle being rotated at a low speed. In this case, the central portion B of the bottle is detected in a vertical direction. A concrete example of the method will be described with reference to FIG. 9. Both sides of each of empty bottles 4 conveyed by a bottle conveyer 22 are held by endless belt type bottle carriers 23 and 24. As the drive speed of the bottle carrier 23 is higher than that of the bottle carrier 24, each empty bottle 4 is conveyed on while being slowly rotated as indicated by the arrow C. A plurality of (for instance four) CCD cameras 25 are disposed at a predetermined intervals on one side of the area where the bottle 4 is rotated as described above. The CCD cameras 25 inspect only the central portion of the bottle 4 for the magnitudes of light quantities passed through the bottle 4 from the light source 1. Accordingly, the entire circumferential surface of the bottle 4 can be inspected while the bottle 4 makes one (or a half) revolution.

A foreign matter on a bottle may be one such as cellophane which is optically anisotropic and transparent. A foreign matter detecting device for detecting such a foreign matter will be described.

Figure 10:
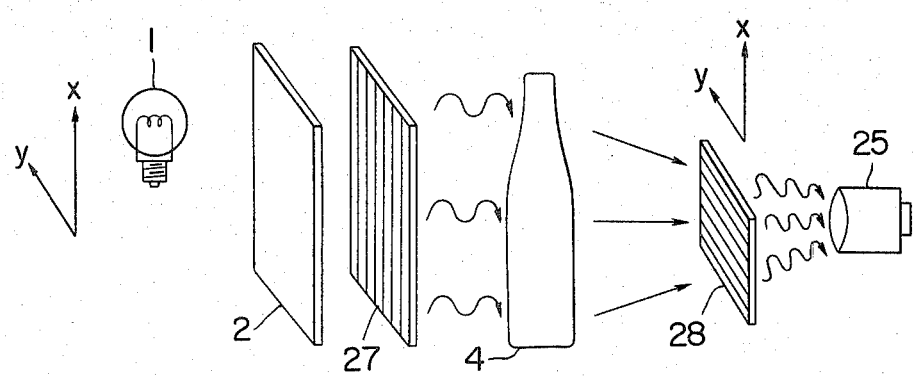
FIG. 10 is a diagram showing another embodiment of the invention.

As shown in FIG. 10, light from a light source 1 is diffused by a diffusing plate 2. The resultant diffusion light is polarized by a polarization filter 27 having, for instance, a plane of polarization in the y-axis direction. The light thus treated is irradiated on a bottle 4. Light passed through the bottle 4 is polarized again by a polarization filter 28 which has a plane of polarization orthogonal with that of the above-described polarization filter 27, and is then applied to a CCD camera 25. A video detection signal outputted by the CCD camera 25 is subjected to comparison and discrimination by the video signal processing device 13 as shown in FIGS. 3 and 4, so that the presence or absence of a transparent material such as cellophane sheet is detected.

If a foreign material such as a cellophane sheet is stuck on the bottle body, the polarized light applied to the bottle 4 is scattered by the foreign matter. This scattered light passes through the polarization filter 28 whose polarization plan is orthogonal with that of the polarization filter 27. Therefore, transparent foreign matters or contaminants can be detected by detecting the transmitted light with the CCD camera 25.

Figure 11:
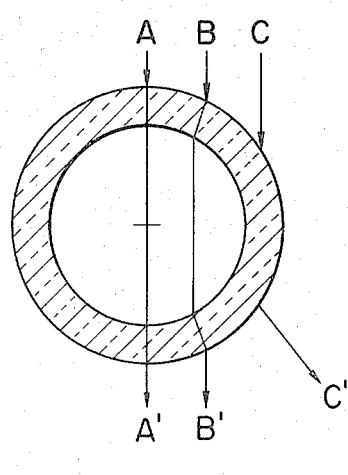

By the way, the light transmitting paths are detected using laser to tell the quality of the transmitting light shown in FIG. 11. In FIG. 11, light A penetrates in the direction of A' to the photoelectric conversion device, but light C does not. As a matter of practice, however, since the diffusion light is applied to the bottles to be inspected, part of the transmitted light reaches the photoelectric conversion device.

Figure 12:
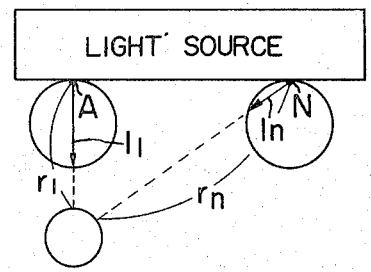
FIGS. 11 through 13 are explanatory diagrams for generating of the principle of an inspection region signal according to this invention, respectively.

The distribution of the diffusion light is shown by vector as shown in FIG. 12. The diffusion light perpendicular to the diffusing plate is strong and the one diagonal to the plate is weak, making the distribution circular.

The light coming from the direction of A is $I_l/r_l^2$ with the distance r between the diffusing plate and the bottle to be inspected, and takes the shortest path through the thickness of the bottle to the photoelectric conversion device. The light coming from the direction N is $I_n/r_n^2$, which is rather weak, and takes a longer path through the thickness of the bottle, part of the light reaching the photoelectric conversion device.

Based on such optical system, no shade is generated at the vertically central region of a bottle, but at the periphery thereof shades are generated due to decreases of transmitted light caused by light deflection of glass wear.

Figure 13:
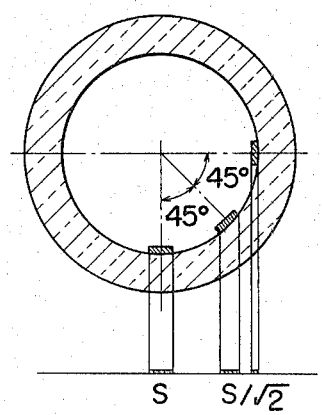

As shown in FIG. 13, the detection accuracy for the detection solely by a photoelectric conversion device without causing the bottles to rotate is high at their vertically central portions and low, at their peripheries; as shown in FIG. 13, a foreign matter with size S is $S/\sqrt{2}$ at the angle of 45° and is isometric at the right angle, because the photoelectric conversion device such as a TV camera converts solid images to plan ones on its photoelectric conversion surface.

Accordingly, the inspection accuracy becomes lower at the peripheries of bottles due to light deflection or long light paths through the thicknesses of bottles.

According to the present invention, inspection only at the vertically central portion of bottles without causing them to rotate makes the detection accuracy uniform.

From the above-mentioned reasons, the present invention limits the inspection region to the vertically central portion of the bottles to be inspected where their images are detected with high inspection accuracy.

According to the above-mentioned fact, another embodiment of the invention, in which the inspection is carried out by automatically determining the inspection region of an object to be inspected, will be described, with reference to FIG. 14.

Figure 14:
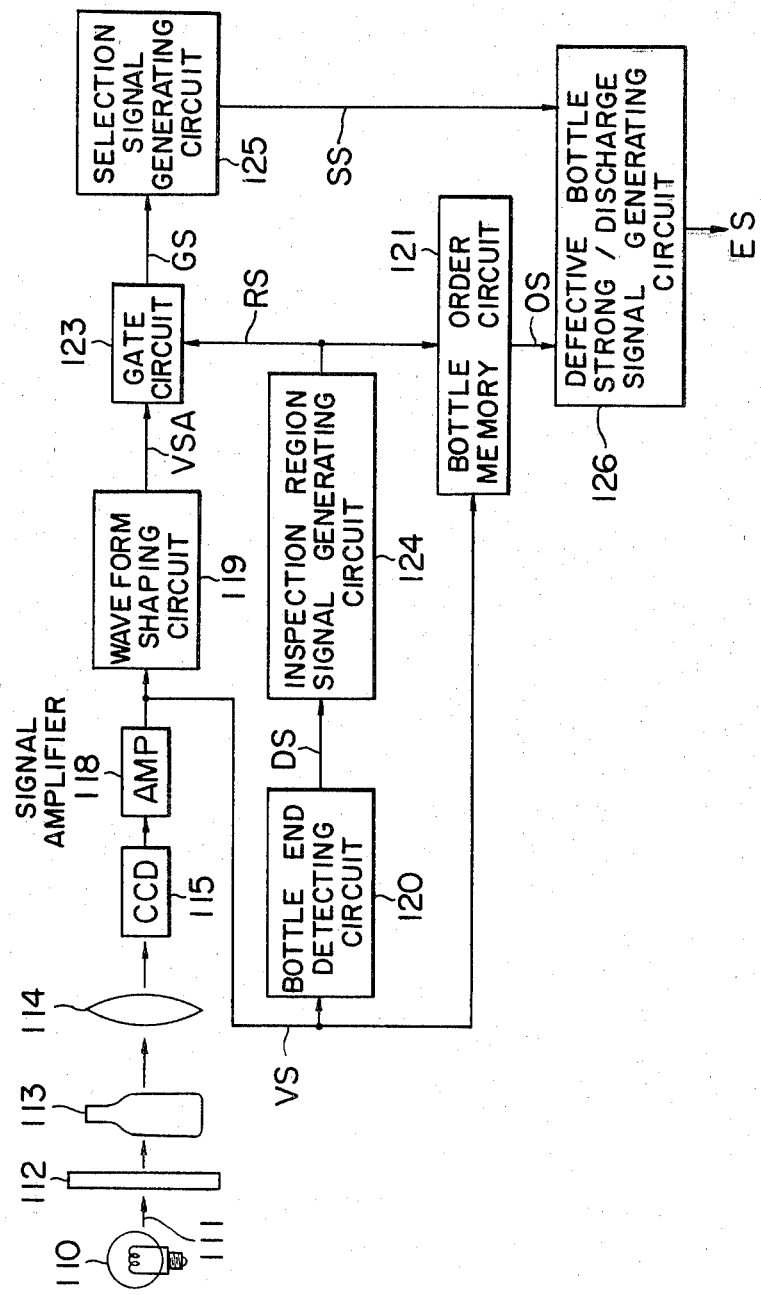
FIG. 14 is a diagram showing a further embodiment of the invention.

In FIG. 14, reference numeral 110 designates a light source incorporated in the foreign matter detecting device according to the invention. Light 111 from the light source 110 is uniformly diffused by a diffusion plate 112, and is then applied to bottles 113 to be inspected which are continuously conveyed by a conveyor (not shown). Light passed through the bottle 113 is condensed by a condenser lens 114 and is then applied to a two-dimensional CCD 115 serving as a photoelectric conversion device. The CCD 115 is provided with a synchronous signal generating circuit and has a number of CCD elements 116 (FIG. 15). Scanning of the CCD elements 116 is effected in the direction of the arrow A corresponding to the axis of the bottle 113, more specifically along the arrows a, b, c, . . . in the stated order, from left to right (in the direction of the arrow B).

Video signals outputted by the elements 116 of the CCD 115 are amplified by a signal amplifier 118 and are then applied to a waveform shaping circuit 119 adapted to shape the waveform of a foreign matter signal included in a video signal VS, to a bottle end detecting circuit 120 adapted to detect the end portion of a bottle 113 to be inspected, and to a bottle order memory circuit 121 adapted to store the order of bottles delivered to the inspection section. The waveform shaping circuit 119, having a signal level comparison circuit, detects a foreign matter signal out of the video signal VS (FIG. 16) and shapes it, to provide a video waveform signal VSA. The signal VSA thus shaped is applied to a gate circuit 123.

The bottle end detecting circuit 120 detects the position of the end of a bottle 113 with the aid of the video signal from the CCD 115 to provide a detection signal DS which is applied to an inspection region signal generating circuit 124. These circuits 124 and 120 form an inspection region determining circuit which determines an inspection region with the aid of the bottle end detection signal DS from the bottle end detecting circuit 120, thereby to provide an inspection region signal RS which is applied to the gate circuit 123 and the bottle order memory circuit 121.

More specifically, in the bottle end detecting circuit 120, the large (decreasing) variation in level of the video signal VS caused by the presence or absence of a bottle is detected by a differentiation comparator or the like to provide the bottle end signal (FIG. 17). This signal is converted into the pulse DS (FIG. 18) having a predetermined time width by using a one-shot multivibrator or the like, the pulse DS being delivered to the inspection region signal generating circuit 124. In response to the trailing edge of the pulse DS, the inspection region signal RS (FIG. 19) corresponding to the substantially central portion of a bottle is generated. The inspection region signal RS has a time width corresponding to, for instance, two columns of elements 116 extending along the axis of a bottle. By the inspection region signal RS, the central belt-shaped region extending along the axis of the bottle 113 can be taken as the inspection region (width). The delay time (pulse width) provided by the one-shot multi-vibrator can be suitably determined by controlling the time constant of a circuit formed with a capacitor C and a resistor R. Thus, a variety of bottles different in size can be inspected.

The gate circuit 123 receives the inspection region signal RS, and the video waveform signal VSA from the waveform shaping circuit 119. However, the gate circuit 123 passes (picks up) only the video waveform signal VSA corresponding to the inspection region signal RS, among the video waveform signals VSA applied thereto, thereby to provide a waveform signal (pick-up signal) GS which is applied to a selection signal generating circuit 125. This circuit 125 operates to detect the video waveform signal GS delivered from the gate circuit 123 to discriminate whether the bottle under inspection is acceptable or not, to provide a discrimination (selection) signal SS which is applied to a defective bottle storing and discharge signal generating circuit 126.

The circuit 126 receives the bottle order signal OS from the bottle order storing circuit 121. When the images of plural bottles 113 are projected onto the CCD 115 simultaneously, the bottle order storing circuit 121 stores the inspection order of the bottles 113 by receiving the synchronous signal included in the video signal VS and the inspection region signal RS from the inspection region signal generating circuit 124, thereby to apply the bottle order signal OS to the defective bottle storing and discharge signal generating circuit 126. During the period of delivering the bottle order signal OS from the bottle order storing circuit 121, the circuit 126 stores the presence or absence of the selection signal provided by the selection signal generating circuit 125, and outputs a discharge signal ES when the selection signal SS reaches a predetermined value. With the aid of this discharge signal ES, the bottle is automatically discharged from the bottle inspection line when it is delivered to the discharge outlet.

The action of the detecting device thus organized will be described.

The light 111 from the light source 110 is uniformly diffused by the diffusion plate 112 and is then irradiated on the bottle 113 to be inspected. The light passed through the bottle 113 forms the image of the bottle on the CCD 115 by means of the lens 114. The light is greatly absorbed when pased through the bottle 113. Accordingly, the formed image of the bottle is such that the light transmission portion of the bottle is greatly different from the order portion in light quantity and the central portion is relatively light while the peripheral portion is relatively dark because of the refractive index and configuration of the bottle. Such an optical image is converted into an electrical signal by the CCD 115 as shown in FIG. 16. As is apparent from FIG. 16, the output level of the video signal VS for the central portion of the bottle is relatively flat and substantially constant, but it is smaller toward the both ends. Accordingly, the output variation of the video signal VS caused by the presence or absence of foreign matter on a bottle 113 is larger for the central portion of the bottle, but it is smaller for the peripheral portion. Thus, it is considerably difficult to distinguish a foreign matter from glass in the peripheral portion of the bottle. The inspection of the central portion of a bottle is scarcely affected by characters curved in relief and marks on the bottle and by the uneven wall thickness and the joint of the bottle in the circumferential direction thereof. This is due to the fact that when light is irradiated on a bottle in a direction perpendicular to the surface thereof, the difference in light quantity due to the non-uniform wall thickness of the bottle or the like is small. However, when a bottle is irradiated by light in a direction oblique to or in parallel with the axis or surface of the bottle, then the optical transmission path is increased, and the light is greatly absorbed or refracted, i.e. the quantity of light passed through the bottle is considerably decreased.

Accordingly, in order to effectively inspect bottles for foreign matters (including scratches also) with high accuracy, it is necessary that the direction of scanning (having a short repetitive scanning period) of the CCD 115 is substantially the same as (in parallel with) the axial direction of a bottle 113 and the inspection region is limited to the central region (indicated by the hatching lines in FIG. 15) of the bottle 113. This invention can automatically determine the most suitable inspection region of a bottle.

When in the bottle end detecting circuit 120 the output level of the video signal VS becomes abruptly lower than a preset value as shown in FIG. 16, the bottle end signal is produced. With the aid of the bottle end signal, the inspection region signal generating circuit provides the inspection region signal RS in response to the pulse waveform signal from the delay circuit such as a one-shot multivibrator (not shown). The inspection region signal RS is applied to the gate circuit 123. During the application of the signal RS, the gate circuit 123 passes only the video digital signal VSA from the waveform shaping circuit 119, the signal VSA being applied to the selection signal generating circuit 125. In other words, the gate circuit 123 delivers only the video digital signal VSA corresponding to the inspection region signal to the selection signal generating circuit 125, where the video digital signal is selected, and the selection signal SS is produced when a foreign matter is on the bottle.

On the other hand, when the images of a plurality of bottles 113 are simultaneously projected onto the CCD 115, the vertical synchronizing signal is detected from the video signal VS delivered to the bottle order storing circuit 121. With reference to the synchronizing signal, the inspection region signals RS from the inspection region signal generating circuit 124 are put in order and are then applied to the defective bottle storing and discharge signal generating circuit 126. This circuit 126 operates as follows: The circuit 126 detects for what bottle the selection signal (foreign matter signal) SS from the selection signal generating circuit has provided. When the bottle includes a foreign matter, then the discharge signal generating circuit 126 outputs the discharge signal ES in synchronization with a detection signal outputted by a bottle arrival detector provided in the vicinity of the defective bottle discharge outlet when the bottle reaches the latter, so that a discharge mechanism (not shown) is operated to remove the defective bottle from the bottle inspection line.

In the embodiment described above, the central belt-shaped portion of a bottle, which is extended along the axis of the bottle, is employed as the inspection region; however, depending on the configuration of a bottle to be inspected, only the region of the bottle perpendicular to the axis of the bottle may be automatically detected, or the entire region of the bottle may be detected.

Furthermore, the detection signal DS of the bottle end detection circuit 120 may be detected from one CCD element where the output level variation of the video signal VS is firstly caused, or may be detected when the output level reaches a predetermined number of CCD elements. In addition, the bottle end detection signal may be detected from the particular CCD elements along the horizontal scanning direction (or the direction B) as indicated by the line A—A' in FIG. 15.

The inspection region signal RS shown in FIG. 19 may be produced directly from the bottle end detection signal, without interposing the pulse waveform signal shown in FIG. 18, or may be produced in synchronization with the horizontal synchronizing signal driving the CCD.

Figure 20:
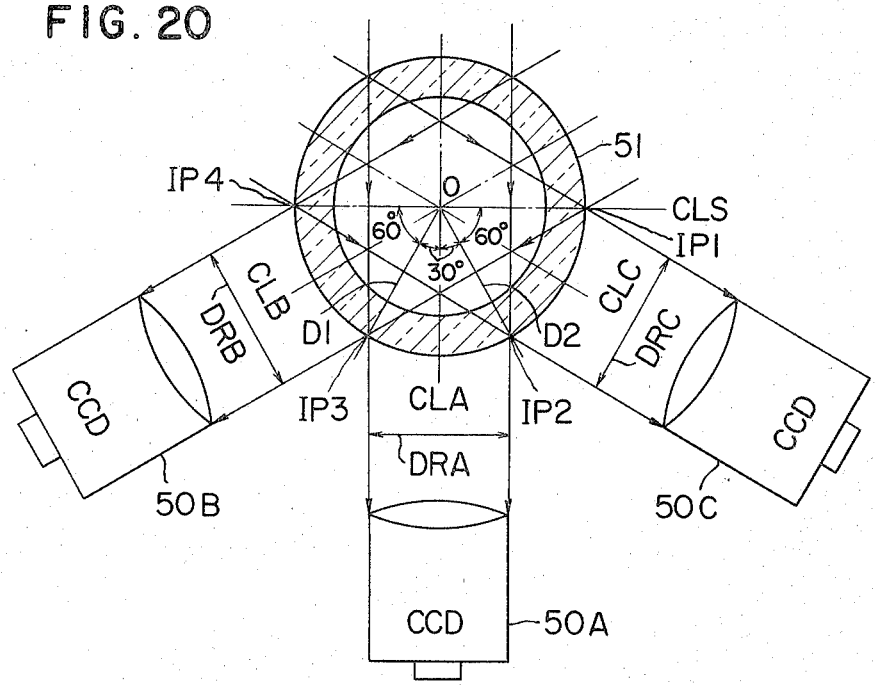
FIG. 20 shows inspection conditions of the apparatus provided with three CCD cameras.

For the detection of the axially central inspection region of a bottle to be inspected the whole bottle can be accurately inspected without being rotated by installing a plurality of CCDs and deciding their appropriate scanning regions. FIG. 20 shows one example of inspection in which three CCDs 50A, 50B and 50C are used.

In FIG. 20, the semi-circumference (180°) of a bottle 51 to be inspected divided by the central line CLS passing the axis O thereof, along which three CCDs are installed is divided into three by the dividing lines $D_1$ and $D_2$ and the central line CLS. Next decided are the points IP1–IP4 where the dividing lines $D_1$ and $D_2$ intersect with the semi-circumference of the bottle 51. Then, a first CCD 50C is installed so as to scan the circumference of the bottle 51 between the points IP1 and IP2 along the center line CLC which bisects the circumference therebetween passing the axis of the bottle 51. A second CCD 50C is placed so as to cover the circumference between the points IP2 and IP3 along the center line CLA; a third CCD 50B disposed so as to cover the circumference between the points IP3 and IP4 along the center line CLB. At the same time, the above-mentioned inspection region signal generating circuit 60 decides the inspection region DRC between the points IP1 and IP2 for CCD 50C; DRA between the points IP2 and IP3 for CCD 50A; DRB between the points IP3 and IP4 for CCD 5B. Thus, the installation of three CCDs 50A, 50B and 50C and defining the inspection regions for the CCDs make it possible for the bottle 51 to be completely inspected, without being rotated, with the lines CLA, CLB and CLC, at the centers of the inspection regions.

Figure 21:
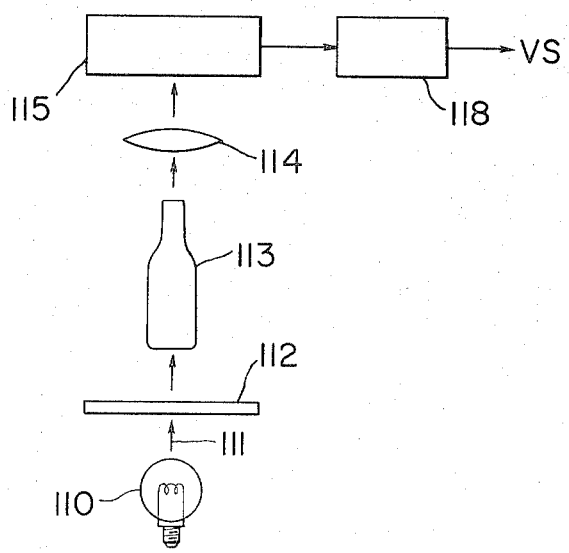
FIG. 21 is a block diagram showing another embodiment of the invention.

The case where the inspection region is determined in a direction in parallel with the axis of a bottle to detect the foreign matter, has been described above. However, the foreign matter can be detected by determining the inspection region in a direction perpendicular to the axis of a bottle. In this case, an arrangement of applying light to bottles continuously conveyed by a conveyor and receiving light passed through the bottles is as shown in FIG. 21.

A condenser lens 114 is provided above the bottle 113, and a diffusion plate 112 is provided below the bottle 113. Light from a light source provided below the diffusion plate 112 is applied through the bottle 113 to a CCD 115 provided above the lens 114. The process of the output signal of the CCD 115, after being amplified by an amplifier 118, is substantially equal to that in the above-described embodiment in which the inspection region is in parallel with the axis of a bottle to be inspected. In this case, the image of the bottle 113 formed on the elements 116 of the CCD 115 is as shown in FIG. 22, and its video signal VS is as shown in FIG. 23. The great variation of the output level of the video signal VS is detected by the bottle end detecting circuit 120 with respect to its increase and decrease directions as indicated in FIG. 24, thereby to provide the bottle end detection signal DS which is applied to the inspection region signal generating circuit 124. In this circuit 124, a signal which is set by a pulse $P_1$ of the bottle end detecting signal DS corresponding to the decrease direction of the video signal VS and reset by a pulse $P_2$ corresponding to the increase direction of the video signal VS is formed to be employed as an inspection region signal RS (FIG. 25), whereby an inspection surface perpendicular to the axis of the bottle can be determined to detect a foreign matter on the bottom of the bottle 113.

The detection of a foreign matter vertical to the axis of the bottle to be inspected creates remarkable differences in the quantity of transmitted light between the peripheral portion and the central portion of the bottle. Since the peripheral portion is generally dark, and the central portion of the bottle bottom is generally light, it makes impossible to detect the whole bottle for a foreign matter using same two threshold values. Such difficulty is eliminated by forming a link-shaped inspection region signal RG1 conforming to the shape of the edge of the bottle and a circular inspection region signal RG2 conforming to the shape of the bottom surface of the bottle as shown in FIG. 26.

Figure 26:
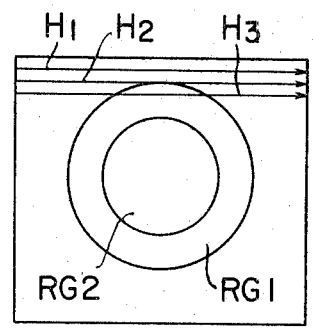
FIG. 26 shows another example of the inspection region according to this invention.

Next, it will be explained how to form the inspection region signals RG1 and RG2 as shown in FIG. 26.

Figure 27:
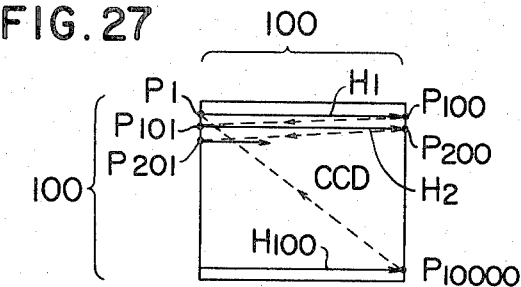
FIGS. 27 through 29 and FIGS. 31 through 33 are explanatory diagrams for inspection region signal corresponding to FIG. 26.

A way of scanning by a CCD composed of $100 \times 100$ elements and clock pulse is as shown in FIG. 27.

The whole bottle to be inspected is horizontally inspected by scanning lines $H_1, H_2, \ldots, H_{100}$. Scanning in one field takes places at the initial position $P_1$ in the horizontal direction as shown by a scanning line $H_1$, and when the scanning line $H_1$ reaches the end position $P_{100}$ thereof, the scanning line is caused to return to the starting position of the subsequent scanning line $H_2$ by the timing signal inputted from a driving circuit (not shown). The scanning continuous in the horizontal direction as shown by the scanning line $H_2$ to the end position $P_{200}$ thereof, where the scanning line is caused to go back to the starting position $P_{201}$ of the subsequent scanning line $H_3$ as happened to the scanning line $H_1$ at its end position $P_{100}$. The scanning goes on, repeating the same action until the last scanning line $H_{100}$ arrives at the terminal position $P_{10000}$, where the scanning line is caused to return to the initial position $P_1$ of the scanning by the timing signal inputted from the driving circuit. In such manner, fields of scanning are repeatedly formed.

Figure 28:
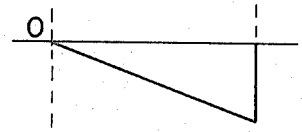
Figure 29:
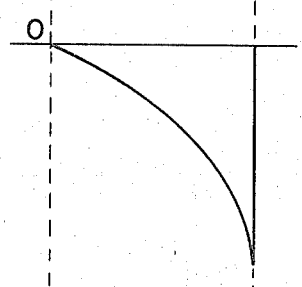
Figure 30:
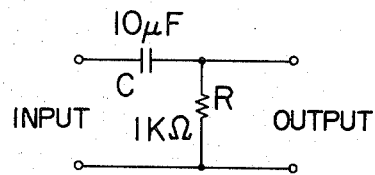
FIG. 30 is a circuit which is used to generate a waveform signal as shown in FIGS. 31 and 32.
Figure 31:
Figure 32:
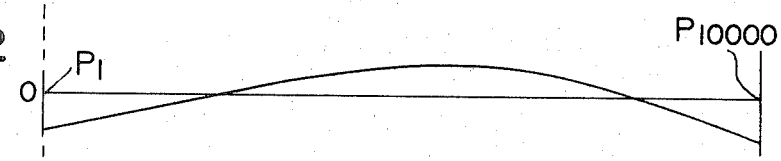
Figure 33:
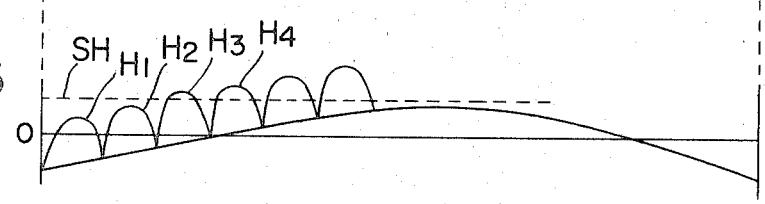

In the scanning action, a sawtooth wave as shown in FIG. 28 is formed in synchronization with each of the scanning lines $H_1, H_2, \ldots, H_{100}$. The sawtooth wave is integrated to a wave as shown in FIG. 29. Further, the wave is inputted to a direct current component breaking circuit as shown in FIG. 30 to obtain a parabolic wave as shown in FIG. 31. In synchronization with the scanning from the initial position $P_1$ to the terminal position $P_{10000}$, a parabolic wave as shown in FIG. 32 is formed. The wave shown in FIG. 32 is synthesized with the wave shown in FIG. 31 of each scanning line to obtain the wave as shown in FIG. 33. Then, the wave obtained in such way is quantized to binary with the threshold level SH and the inspection region as shown in FIG. 26 is obtained.

Figure 34:
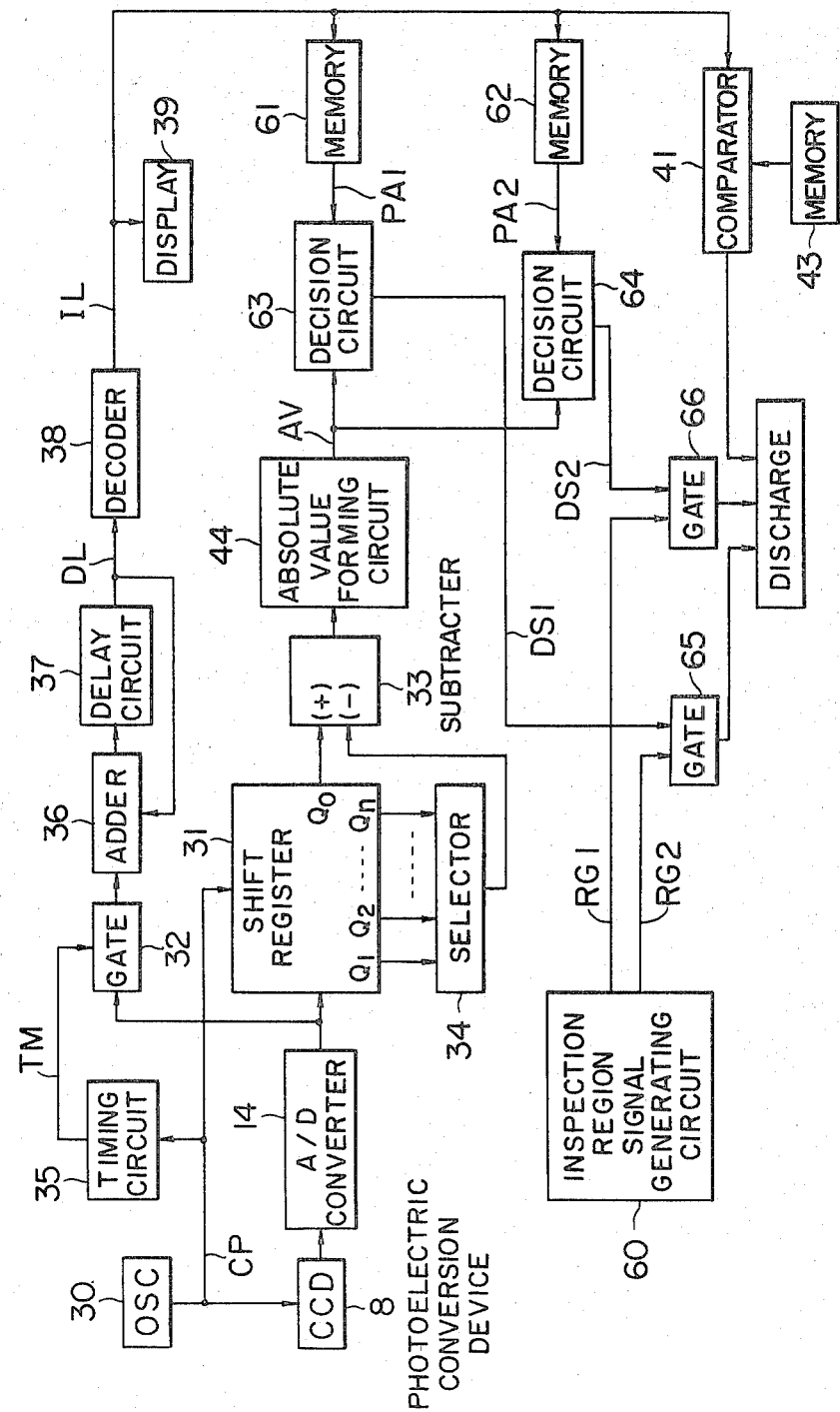
FIG. 34 is a block diagram showing still another embodiment of the invention.

FIG. 34 shows one example of the foreign matter detecting device which uses the inspection region signal of the peripheral and the central portion of the bottom of a bottle to be inspected, corresponding to the circuit shown in FIG. 4. This device includes an inspection region signal generating circuit 60 which forms and outputs the inspection region signals RG1 and RG2 as mentioned above as well as two memories 61 and 62. The memory 61 stores data corresponding to the relatively light center of a bottle bottom and the memory 62 stores data corresponding to the dark region of the bottle. The presence or absence of a foreign matter at the central portion of the bottle bottom is decided by a decision circuit 64, while the decision signals DS1 and DS2 generated thereby are inputted to gates 65 and 66, respectively. The inspection region signals RG1 and RG2 from the inspection region signal generating circuit 60 are also inputted to another input terminal of the gates 65 and 66, respectively. Only when the inspection region signals RG1 and RG2 coincide with the decision signals DS1 and DS2, the relevant bottle is caused to be discharged.

In the above-described embodiment, light is irradiated from below a bottle to be inspected and is received from above the bottle; however, the invention is not limited thereto or thereby. That is, light may be irradiated from above a bottle to be inspected and received from below the bottle.

In the above-described embodiments, the photo-electric conversion is the two-dimensional CCD; however, it may be a non-accumulation type image pickup tube. Furthermore, objects to be inspected by the foreign matter detecting device are not limited to bottles.

As is clear from the above description, the foreign matter detecting device according to the invention is so simple in construction and low in manufacturing cost that among the detection signals from the photoelectric conversion device comprising the CCD the variations in magnitude of detection signals corresponding to variable two adjacent points are successively detected by the video signal processing device to positively detect the presence or absence of foreign matters or cracks or scratches on bottles. Furthermore, with the foreign matter detecting device, foreign matters on a bottle can be automatically detected, which will considerably contribute to labor saving in inspecting bottles.

In addition, according to the invention, the inspection region determining circuit automatically determines the inspection region in a direction perpendicular to or in parallel with the axis of a bottle to be inspected from the video output signal which is provided by the photoelectric conversion device according to the presence or absence of an object such as a bottle to be inspected. Therefore, the most suitable inspection region can be automatically detected, and the surface of the object, which is most suitable for inspection, can be inspected. Accordingly, the inspection speed of objects to be inspected is increased, and the inspection accuracy is considerably improved.

What is claimed is:

1. A device for detecting a foreign matter on an object such as a bottle to be inspected which comprises a light source from which light is applied to said object; a photoelectric conversion device having a number of light receiving elements to which light passed through said object is applied; and a video signal processing device for successively subjecting to comparison and discrimination of detection signals each of which is detected at variable two adjacent points of said object thereby, said video signal processing device discriminating the variations in magnitude of said detection signals at said variable two adjacent points to detect the presence or absence of a foreign matter on said object.

2. A device as claimed in claim 1, wherein said video signal processing device comprises:
   an analog-to-digital converter for converting an output signal of said photoelectric conversion device into a digital signal;
   a register means inputting said digital signal and outputting a delay signal variously delayed by selecting a comparison distance of two adjacent points which are subjected to comparison and discrimination;
   a subtracting means for obtaining an absolute value of a difference between said delay signal and said digital signal;
   an adding means for successively adding said digital signal during a predetermined gate time and for outputting a transmitted light signal;
   a first memory for outputting a permissive value which is stored in advance, corresponding to the magnitude of said transmitted light signal; and
   a decision circuit for deciding presence or absence of foreign matter in said object according to comparison between the absolute value and the permissive value.

3. A device as claimed in claim 1, wherein a plurality of photoelectric conversion devices are arranged so as to form a predetermined angle with respect to said object to detect said object in its entirety.

4. A device as claimed in claim 1, wherein said object is conveyed with rotation and is inspected while said object makes at least a half revolution.

5. A device as claimed in claim 2, wherein said video signal processing device further includes a second memory for outputting a minimum transmitted light value which is stored in advance, and a comparator for comparing said transmitted light signal with the minimum transmitted light value and for outputting a discharge signal when said transmitted light signal is lower than the minimum transmitted light value.

6. A device as claimed in claim 1, 2, 3, 4 or 5, wherein said photoelectric conversion device comprises a charge coupled device.

7. A device for detecting a foreign matter on an object such as a bottle to be inspected through a polarization filter which comprises a light source from which light is applied to said object; a photoelectric conversion device having a number of light receiving elements to each of which light having passed through said object is applied through another polarization filter which is orthogonal with said polarization filter; and a video signal processing device for successively subjecting to comparison and discrimination detection signals of said photoelectric conversion device which correspond to variable two adjacent points detected thereby, said video signal processing device discriminating the variations in magnitude of said detection signals corresponding to said variable two adjacent points to detect the presence or absence of a foreign matter such as a cellophane sheet on said object, which is optically anisotropic and transparent.

8. A device as claimed in claim 7, wherein said photoelectric conversion device comprises a charge coupled device.

9. A foreign matter detecting device comprising:
a photoelectric conversion device having a number of photoelectric conversion elements on which an optical image of an object such as a bottle to be inspected is formed, and converting said optical image into an electrical signal;
a level detecting circuit for detecting an output level of a video signal which is provided by said photoelectric conversion device according to the presence or absence of said object;
an inspection region determining circuit for determining from said video signal provided by said photoelectric conversion device an inspection region in parallel with the axis of said object; and
a selection circuit for picking up an output signal of said level detecting circuit which corresponds to an inspection region signal provided by said inspection region determining circuit, to provide a selection signal which is utilized to discriminate whether or not said object has a foreign matter.

10. A device as claimed in claim 9, wherein said photoelectric conversion device comprises a charge coupled device.

11. A device as claimed in claim 9 or 10, wherein a plurality of photoelectric conversion devices are arranged so as to form a predetermined angle with respect to said object to detect said object without rotation in its entirety.

12. A device as claimed in claim 9 or 10, wherein said object is conveyed with rotation and is inspected while said object makes at least a half revolution.

13. A foreign matter detecting device comprising:
a photoelectric conversion device having a number of photoelectric conversion elements on which an optical image of an object such as a bottle to be inspected is formed, and converting said optical image into an electrical signal;
a level detecting circuit for detecting an output level of a video signal which is provided by said photoelectric conversion device according to the presence or absence of said object;
an inspection region determining circuit for determining from said video signal provided by said photoelectric conversion device an inspection region in a direction perpendicular to the axis of said object; and
a selection circuit for picking up an output signal of said level detecting circuit which corresponds to an inspection region signal provided by said inspection region determining circuit, to provide a selection signal which is utilized to discriminate whether or not said object has a foreign matter.

14. A device as claimed in claim 13, wherein said photoelectric conversion device comprises a charge coupled device.

15. A device for detecting a foreign matter on a bottom of an object such as a bottle to be inspected, which comprises:
a light source from which light is applied to said object;
a photoelectric conversion device having a number of light receiving elements to which light passed through said bottom is applied;
an analog-to-digital converter for converting an output signal of said photoelectric conversion device into a digital signal;
a register means inputting said digital signal and outputting a delay signal variously delayed by selecting a comparison distance of two adjacent points are subjected to comparison and discrimination;
a subtracting means for absolutely subtracting said delay signal from said digital signal;
an adding means for successively adding said digital signal during a predetermined gate time and for outputting a transmitted light signal;
a first memory outputting a first permissive value which is stored in advance and represents a central portion of the bottom, corresponding to the magnitude of said transmitted light signal therein;
a second memory outputting a second permissive value which is stored in advance and represents a peripheral portion of the bottom, corresponding to the magnitude of said transmitted light signal therein;
a first decision circuit for deciding presence or absence of foreign matter in said central portion of the bottom according to comparison between the absolute value and the first permissive value;
a second decision circuit for deciding presence or absence of foreign matter in said peripheral portion of the bottom according to comparison between the absolute value and the second permissive value;
an inspection region signal generating circuit for generating a central inspection region signal corresponding to said central portion of the bottom and a peripheral inspection region signal corresponding to said peripheral portion of the bottom;
a first gate for outputting a first discharge signal according to the central inspection region signal and an output of the first decision circuit;
a second gate for outputting a second discharge signal according to the peripheral inspection region signal and an output of the second decision circuit;
a third memory outputting a minimum transmitted light value which is stored in advance; and
a comparator for comparing said transmitted light signal with the minimum transmitted light value and for outputting a third discharge signal when said transmitted light signal is lower than the minimum transmitted light value.

16. A device as claimed in claim 15, wherein said photoelectric conversion device comprises a charge coupled device.

* * * * *